United States Patent
Lin et al.

(10) Patent No.: US 10,460,999 B2
(45) Date of Patent: Oct. 29, 2019

(54) METROLOGY DEVICE AND METROLOGY METHOD THEREOF

(71) Applicant: TAIWAN SEMICONDUCTOR MANUFACTURING CO., LTD., Hsinchu (TW)

(72) Inventors: Su-Horng Lin, Hsinchu (TW); Chi-Ming Yang, Hsinchu (TW)

(73) Assignee: TAIWAN SEMICONDUCTOR MANUFACTURING CO., LTD., Hsinchu (TW)

(*) Notice: Subject to any disclaimer, the term of this patent is extended or adjusted under 35 U.S.C. 154(b) by 317 days.

(21) Appl. No.: 14/092,256

(22) Filed: Nov. 27, 2013

(65) Prior Publication Data

US 2015/0146841 A1 May 28, 2015

(51) Int. Cl.
*G01N 23/00* (2006.01)
*H01L 21/66* (2006.01)

(52) U.S. Cl.
CPC .................... *H01L 22/12* (2013.01)

(58) Field of Classification Search
CPC ............ G01N 23/083; G01N 23/02; G01N 23/20008; G01N 23/201; H01L 22/12
See application file for complete search history.

(56) References Cited

U.S. PATENT DOCUMENTS

| | | | | |
|---|---|---|---|---|
| 6,272,198 B1* | 8/2001 | Shimura | ............... | G01T 1/2985 378/7 |
| 7,139,365 B1* | 11/2006 | Janik | ...................... | G01N 23/20 378/137 |
| 7,303,132 B2* | 12/2007 | Knowles | ................ | G02B 26/10 235/462.01 |
| 8,059,918 B2* | 11/2011 | Young | .................. | G06T 7/0042 382/294 |
| 2003/0158470 A1* | 8/2003 | Wolters | ................. | A61B 1/043 600/317 |
| 2005/0069082 A1* | 3/2005 | Buijsse | .................... | G21K 7/00 378/43 |
| 2007/0047794 A1* | 3/2007 | Lang | ..................... | G06T 7/0012 382/132 |
| 2008/0219409 A1* | 9/2008 | Ueda | ...................... | G01B 15/02 378/89 |
| 2009/0200604 A1* | 8/2009 | Chidambarrao | .. | H01L 29/78642 257/329 |
| 2010/0008558 A1* | 1/2010 | Baeumer | ................ | A61B 6/405 382/131 |
| 2010/0331782 A1* | 12/2010 | Hendriks | ............. | A61B 5/0066 604/164.12 |

(Continued)

FOREIGN PATENT DOCUMENTS

| | | |
|---|---|---|
| CN | 101261306 A | 9/2008 |
| CN | 101459102 A | 6/2009 |

(Continued)

*Primary Examiner* — Robert H Kim
*Assistant Examiner* — Sean M Luck
(74) *Attorney, Agent, or Firm* — McDermott Will & Emery LLP (57) ABSTRACT

A metrology device includes a light source and an image sensor. The light source is configured for providing an X-ray illuminating a wafer. The image sensor is configured for detecting a spatial domain pattern produced when the X-ray illuminating the wafer.

20 Claims, 4 Drawing Sheets

(56) References Cited

U.S. PATENT DOCUMENTS

| | | | | |
|---|---|---|---|---|
| 2011/0007869 A1* | 1/2011 | Gendreau | ............... | G01N 23/20 |
| | | | | 378/46 |
| 2011/0036360 A1* | 2/2011 | Lang | ...................... | A61B 6/505 |
| | | | | 128/898 |
| 2012/0219916 A1* | 8/2012 | Teshima | ................... | C25D 5/12 |
| | | | | 430/311 |

FOREIGN PATENT DOCUMENTS

| | | |
|---|---|---|
| CN | 101996398 B | 3/2011 |
| TW | 200506357 | 2/2005 |
| TW | 201310560 A | 3/2013 |
| WO | 00/28577 A1 | 5/2000 |

\* cited by examiner

METROLOGY DEVICE AND METROLOGY METHOD THEREOF

BACKGROUND

Technical Field

The present disclosure relates to a metrology device.

Description of Related Art

With the advancement of semiconductor technology, semiconductor devices become increasingly smaller and denser. The increasingly smaller and denser semiconductor devices are difficult to be manufactured and thus have inconsistent quality. Therefore, the semiconductor devices are examined before the semiconductor devices are released.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure. In the drawings.

DETAILED DESCRIPTION

It is to be understood that the following disclosure provides many different embodiments, or examples, for implementing different features of the disclosure. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for the sake of simplicity and clarity.

The terms used in this specification generally have their ordinary meanings in the art and in the specific context where each term is used. The use of examples in this specification, including examples of any terms discussed herein, is illustrative only, and in no way limits the scope and meaning of the disclosure or of any exemplified term. Likewise, the present disclosure is not limited to various embodiments given in this specification.

As used herein, the terms "comprising," "including," "having," "containing," "involving," and the like are to be understood to be open-ended, i.e., to mean including but not limited to. As used herein, "around", "about", "substantially" or "approximately" shall generally mean within 20 percent, in some embodiments within 10 percent, and in another embodiments within 5 percent of a given value or range. Numerical quantities given herein are approximate, meaning that the term "around", "about", "substantially" or "approximately" can be inferred if not expressly stated. The singular forms "a", "an" and "the" used herein include plural referents unless the context clearly dictates otherwise.

Reference throughout the specification to "one embodiment" or "an embodiment" means that a particular feature, structure, implementation, or characteristic described in connection with the embodiment is included in at least one embodiment of the present disclosure. Thus, uses of the phrases "in one embodiment" or "in an embodiment" in various places throughout the specification are not necessarily all referring to the same embodiment. Furthermore, the particular features, structures, implementation, or characteristics may be combined in any suitable manner in one or more embodiments.

Figure 1:
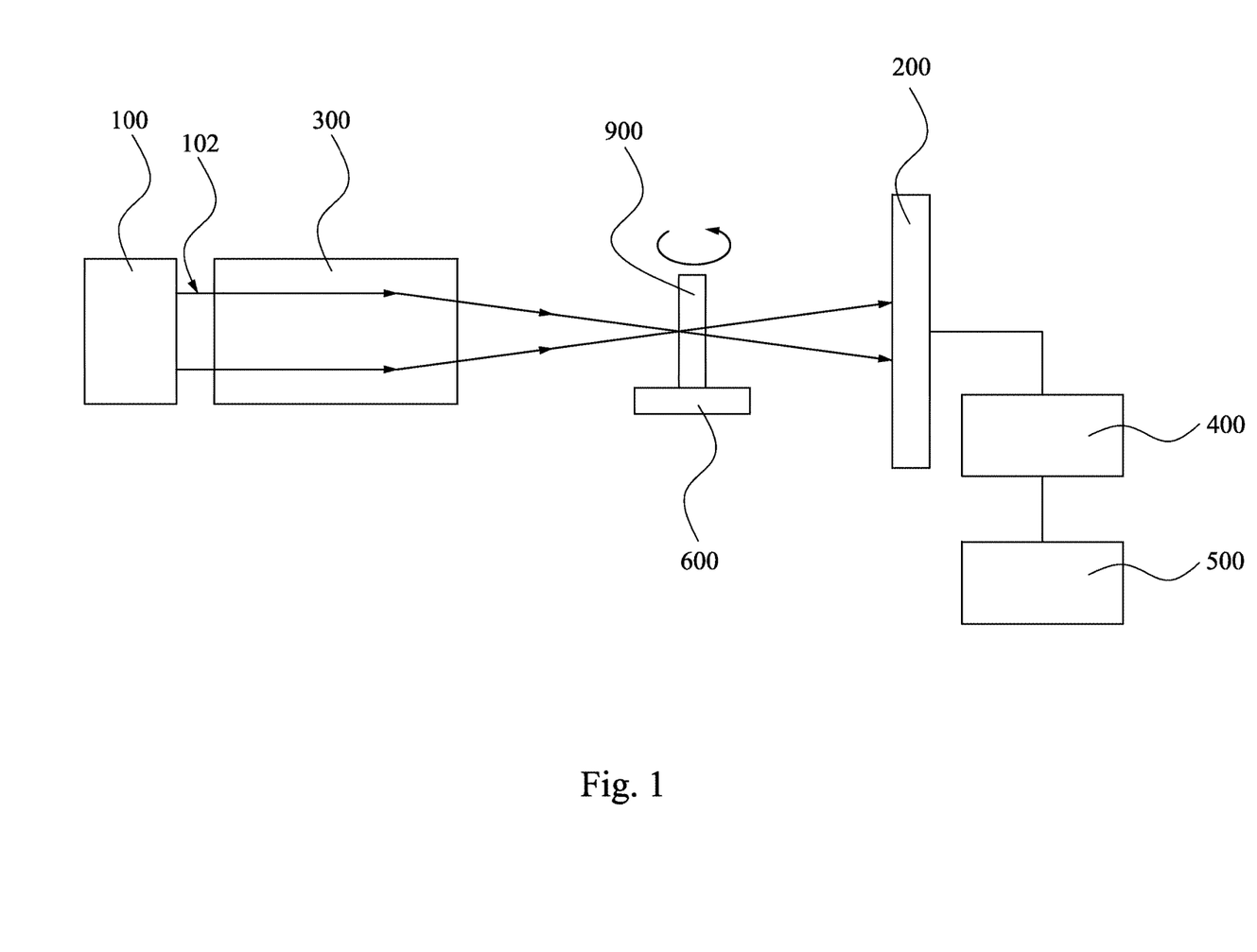
FIG. 1 is a schematic diagram of a metrology device according to one or more embodiments of the present disclosure.

Reference is made to FIG. 1 which is a schematic diagram of a metrology device according to one or more embodiments of the present disclosure. The metrology device includes a light source 100 and an image sensor 200. The light source 100 is configured for providing an X-ray 102 illuminating a wafer 900. The image sensor 200 is configured for detecting a spatial domain pattern produced when the X-ray 102 illuminating the wafer 900.

As such, the metrology device of this embodiment can be utilized to measure smaller scale structures of the wafer 900 since the X-ray 102 has shorter wavelength, and the reliability of the measurement result can be improved.

In one or more embodiments, the light source 100 may be an electromagnetic radiation source. More particular, the light source 100 can be an X-ray source. As a form of electromagnetic radiation, the X-ray 102 may have a wavelength in the range 0.01 to 10 nm corresponding to frequencies in the range 30 petahertz to 30 exahertz ($3 \times 10^{16}$ Hz to $3 \times 10^{19}$ Hz). The wavelength of the X-ray 102 can be shorter than that of ultraviolet light. Since the optical resolution, which can be obtained from Rayleigh criterion, may be about half wavelength of the light beam illuminating to the wafer 900, the optical resolution of the X-ray 102 may be about 0.005 to 5 nm. Taking the wafer 900 having linewidths which are about 20 nm as an example, the optical resolution of the X-ray 102 can be enough to distinguish the morphology of the wafer 900.

In this embodiment, the wafer 900 can be disposed between the light source 100 and the image sensor 200. In other words, the image sensor 200 can detect the X-ray 102 passing through the wafer 900. Therefore, compared to the reflective portion of the X-ray 102, the transmission portion of the X-ray 102 can form a smaller spot size illuminating on the wafer 900, and a smaller scale structure of the wafer 900 can be measured. In addition, although the X-ray 102 passes through the wafer 900 during measurement, the X-ray 102 can not damage the wafer 900.

Furthermore, the power of the X-ray 102 can be larger than 12 kW to pass through the wafer 900. Taking the wafer 900 having a thickness 750 μm for example, the power of the X-ray 102 can be about 13 kW to 14 kW. However, in other embodiments, if the thickness of the wafer 900 has been reduced (such as being polished) before measurement, the power of the X-ray 102 can be smaller than 13 kW. Basically, the power of the X-ray 102 can be depend on the thickness of the wafer 900.

In FIG. 1, the metrology device can further include a lens group 300 for focusing the X-ray 102 to the wafer 900. To measure the smaller scale structure of the wafer 900, the spot size of the X-ray 102 illuminating on the wafer 900 can be smaller. Therefore, the spot size of the X-ray 102 can be reduced by focusing the X-ray 102. In one or more embodiments, the spot size of the X-ray 102 can be about 100 µm. It should be understood that the spot size of the X-ray 102 mentioned above is illustrative only and should not limit the scope of the claimed invention. A person having ordinary skill in the art may select a proper spot size of the X-ray 102 according to actual requirements.

In this embodiment, the lens group 300 can be disposed between the light source 100 and the image sensor 200. More specifically, the lens group 300 can be disposed between the light source 100 and the wafer 900. As such, the X-ray 102 provided by the light source 100 can pass through the lens group 300, being focused by the lens group 300, and then illuminating to the wafer 900. After passing through the wafer 900, the transmission portion of the X-ray 102 can form the spatial domain pattern and then be detected by the image sensor 200.

In one or more embodiments, the metrology device can further include a processor 500 for obtaining the morphology of the wafer 900 according to the detected spatial domain pattern. The type of the processor 500 can depend on the type of the detected spatial domain pattern.

In one or more embodiments, the metrology device may further include a Fourier's transformer 400 for transforming the detected spatial domain pattern into a Fourier frequency domain data, and the processor 500 can obtain the morphology of the wafer 900 according to the Fourier frequency domain data. In greater detail, interference may occur in the transmission portion of the X-ray 102 and form the spatial domain pattern. In other words, the spatial domain pattern can be an interference pattern. The Fourier's transformer 400 can transform the interference pattern into the Fourier frequency domain data, such that the processor 500 can obtain the morphology of the wafer 900 according to the Fourier frequency domain data.

In this embodiment, the Fourier's transformer 400 can be connected to the image sensor 200, and the processor 500 can be connected to the Fourier's transformer 400. However, the claimed scope should be not limited to this respect. A person having ordinary skill in the art may design proper connections among the Fourier's transformer 400, the processor 500, and the image sensor 200 according to actual requirements.

In one or more embodiments, the X-ray 102 may illuminate the wafer 900 from the back side of the wafer 900. It should be pointed out that the back side can be a side opposite to a structure of the wafer 900 which is desired to be measured. After passing through the wafer 900, diffraction may occur within the X-ray 102 due to the interference effect caused from the measured structure of the wafer 900. This portion of the X-ray 102 may undergo destructive or constructive interferences, such that the interference pattern detected by the image sensor 200 may be not so easy to be analyzed in the spatial domain. However, the Fourier's transformer 400 can transfer the interference pattern into the frequency domain, such that some frequency features of the wafer 900 may be shown. The data corresponded to the frequency features can be analyzed using the processor 500, for example, the processor 500 can transfer the data from the frequency domain back to the spatial domain, and the features of the wafer 900 can be obtained.

In some examples, if the structure of the wafer 900 is periodic in the spatial domain, its frequency domain pattern may exist at least one main frequency which is corresponded to the period of the structure. That is, the main frequency is higher if the period of the structure is shorter, and the main frequency is lower if the period of the structure is longer. Therefore, according to the main frequency, the feature of the wafer 900 can be obtained.

In one or more embodiments, the metrology device may further include a rotation mechanism 600 for rotating the wafer 900. The rotating mechanism 600 can be disposed between the lens group 300 and the image sensor 200. However, the claimed scope is not limited to this respect. Through rotating the wafer 900 during measurement, more information of the wafer 900 can be obtained. In greater detail, the X-ray 102 may interact with the electrons and then scatter when it illuminates the wafer 900. If the structure of the wafer 900 is uniform and disordered, the scattered X-ray 102 may be uniformly scattered in the spatial domain. However, if the electron distribution or the structure of the wafer 900 is ordered or regular, the feature of the scattered X-ray 102 may be changed according to the different incident angle of the X-ray 102. Therefore, for rotating the wafer 900 during measurement, the directional features of the wafer 900 can be obtained.

It is understood that the embodiment of the metrology device mentioned above is provided merely as examples and are not intended to be limiting. The metrology device may have different configurations consistent with the spirit of the present disclosure in alternative embodiments depending on design requirements and manufacturing concerns.

Figure 2:
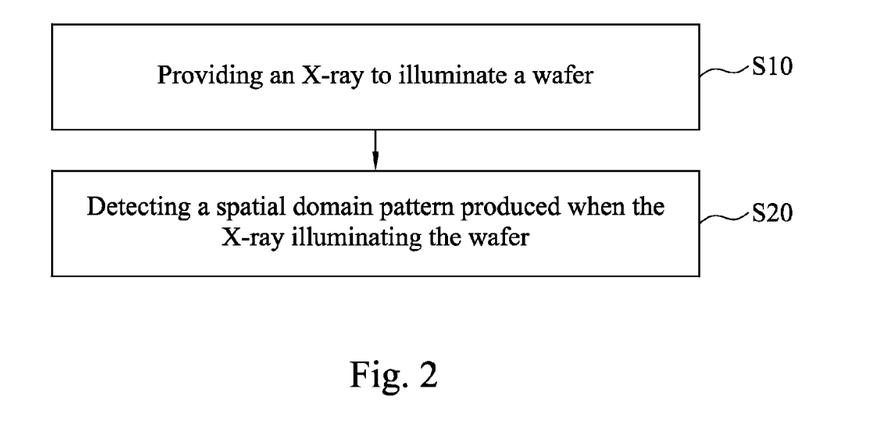
FIG. 2 is a flow chart of a metrology method according to one or more embodiments of the present disclosure.

Another aspect of the present disclosure provides a metrology method for measuring the morphology of a wafer. Reference is made to FIG. 2 which is a flow chart of the metrology method according to one or more embodiments of the present disclosure. To illustrate clarity, the structure of the metrology device in FIG. 1 is applied to the method shown in FIG. 2 in this embodiment. However, the claimed scope is not limited to this respect. The metrology method for measuring the morphology of the wafer 900 includes the following acts:

As shown in act S10, the X-ray 102 is provided to illuminate the wafer 900. Subsequently, as shown in act S20, the spatial domain pattern produced when the X-ray 102 illuminating the wafer 900 is detected. It should be noticed that the flow chart of FIG. 2 shows exemplary acts, but they are not necessarily performed in the order shown. Acts may be added, replaced, changed order, and/or eliminated as appropriate, in accordance with the spirit and scope of disclosed embodiments.

In greater detail, the wavelength of the X-ray 102 can be about 0.01 to 10 nm, such that the optical resolution of the X-ray 102, which may be about 0.005 to 5 nm, can be further improved.

In one or more embodiments, the metrology method may further include act:

focusing the X-ray 102 to the wafer 900.

For example, the spot size illuminating on the wafer 900 may be 100 µm. Therefore, the spot size of the X-ray 102 can be reduced to measure the smaller scale structures of the wafer 900 if the wafer 900 has smaller devices.

Figure 3:
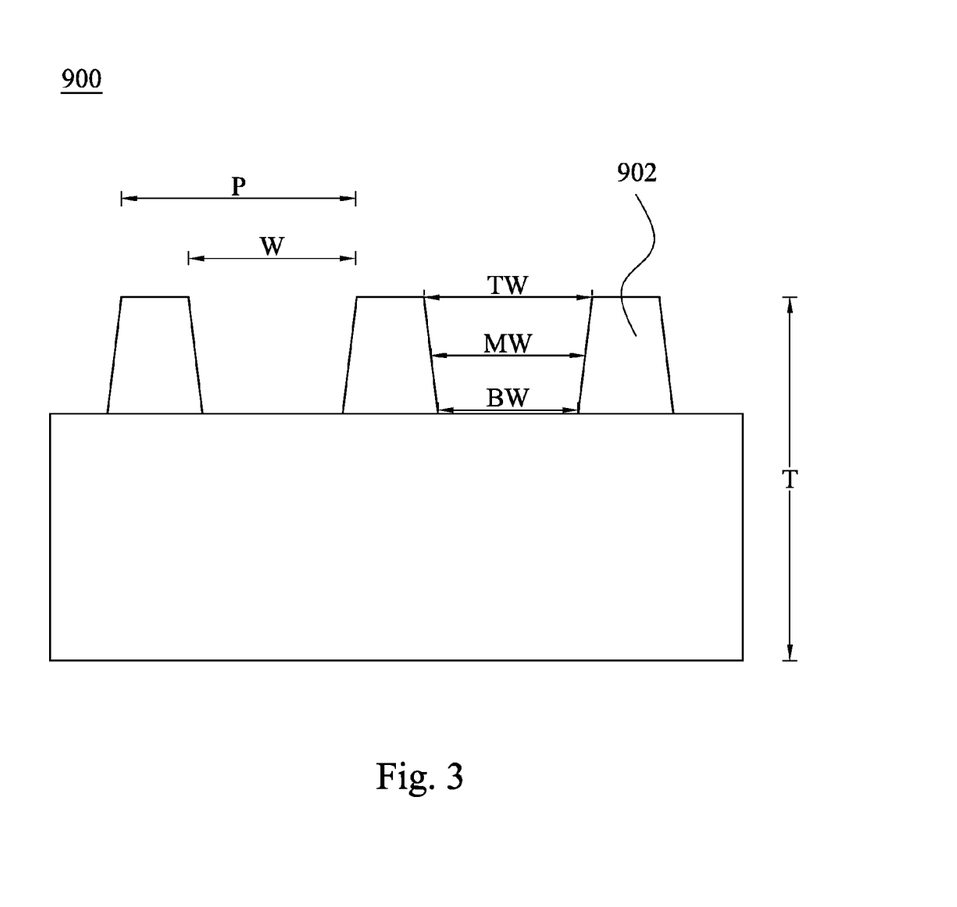
FIG. 3 is a cross-sectional view of the wafer in FIG. 1.
Figure 4:
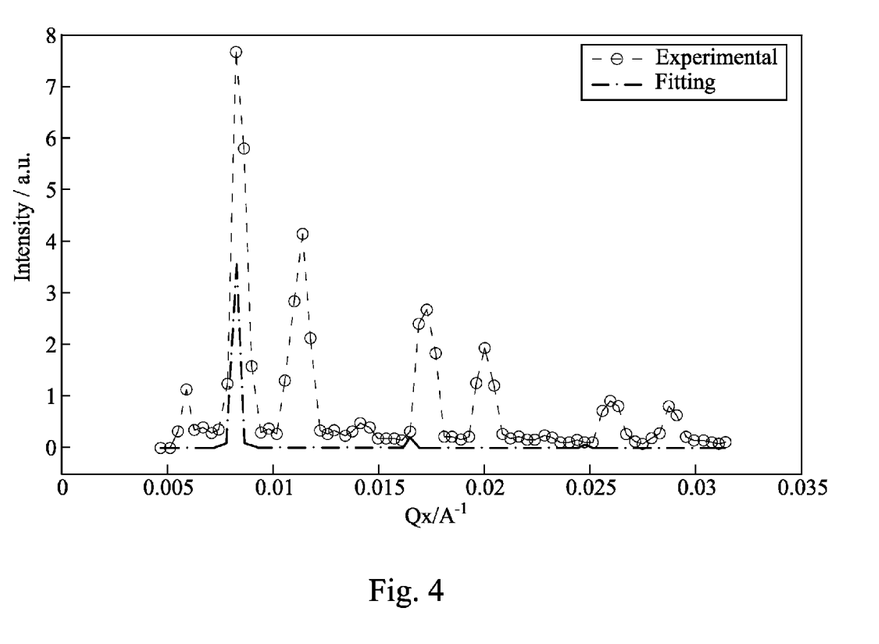
FIG. 4 is a 1D intensity graph of X-ray scattering spectrum measured from the wafer in FIG. 3.

The following paragraphs provide an example with respect to the data of measuring the wafer 900 using the metrology device of FIG. 1. FIG. 3 is a cross-sectional view of the wafer 900 in FIG. 1, and FIG. 4 is an 1D intensity graph of X-ray scattering spectrum measured from the wafer 900 in FIG. 3. Reference is made to FIG. 3 and FIG. 4. In this example, a measured structure 902 of the wafer 900 was a metal layer structure. The thickness T of the wafer 900 was about 750 nm. The wavelength of the X-ray was about 0.1 nm. The power of the X-ray was about 14 kW. The X-ray was incident the back side of the wafer 900 normally, i.e., the incident angle of the X-ray was 0 degrees.

In FIG. 4, the detected spatial domain pattern was the 2D X-ray scattering spectrum (not shown), and the intensity of the 2D X-ray scattering spectrum along x direction was plotted as the "Experimental" curve in FIG. 4. Subsequently, the morphology was obtained. In this example, the "Experimental" curve was fitted to obtain a fitting curve, which was shown in the "Fitting" curve in FIG. 4. According to the "Fitting" curve, main peaks (repeat in scattering vector Qx-0.0083 $A^{-1}$) are obtained. According to the scattering vector, pitch P=75.79 nm was estimated. In addition, average width W=30.46 nm of the measured structure 902 was also estimated. In this example, the values of the pitch P and the average width W of the wafer 900 was smaller than the optical resolution of ultraviolet light, which has wavelength about 150 nm and optical resolution about 75 nm. As such, since the optical resolution of the metrology device in this example was much higher, the metrology device can achieve higher measurement reliability.

In other embodiments, the wafer 900 in FIG. 3 can further be rotated during the measurement, such that more information of the morphology of the wafer 900 can be obtained. For example, top width TW of the measured structure 902, middle width MW of the measured structure 902, and the bottom width BW of the measured structure 902 can be obtained. It should be understood that the feature of the wafer 900 mentioned above is illustrative only and should not limit the scope of the claimed disclosure. A person having ordinary skill in the art may select a proper feature of the wafer 900 to be measured according to actual requirements.

It should be notices that in other embodiments, the measured structure 902 of the wafer 900 is not limited to the structure mentioned above. According to different manufacturing processes, the wafer 900 in FIG. 3 may be a Fin field effect transistor (FinFET), and in other embodiments, the wafer 900 in FIG. 3 may include conductive layers, dielectric layers, and/or semiconductor layers, such that the measured structure can be the morphology of the metal layer of the wafer 900, the morphology of the dielectric layer of the wafer 900, or the morphology of semiconductor layers of the wafer 900.

In greater detail, the conductive layers may include metal layers (the material of which is such as Ag, Au, Cu, etc.), or transparent conductive oxide layers (the material of which is such as ITO, IZO, etc.). The dielectric layer may include oxide layers (such as $SiO_x$), or nitride layers (the material of which is such as $SiN_x$). The semiconductor layers may include nitride silicon layers (the material of which is such as poly-Si, a-Si, etc.). However, the claimed scope should not be limited to the layers mentioned above.

Figure 5:
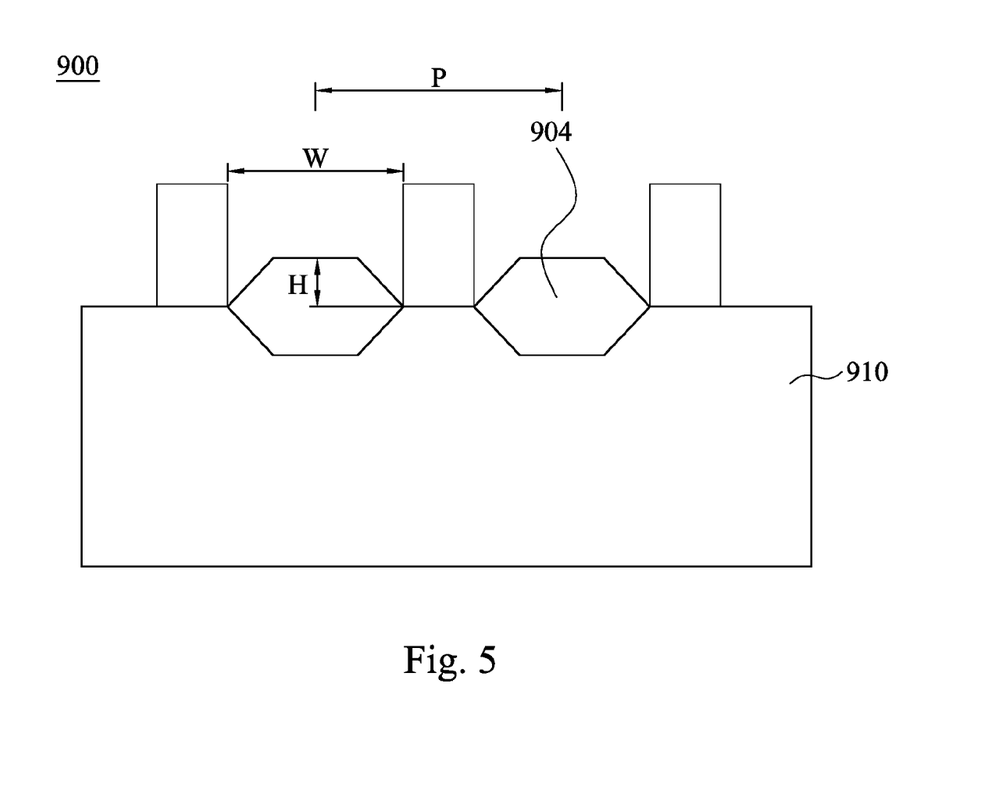
FIG. 5 is a cross-sectional view of the wafer according to one or more embodiments of the present disclosure.

Reference is made to FIG. 5 which is a cross-sectional view of the wafer 900 according to one or more embodiments of the present disclosure. In this embodiment, the wafer 900 can further include raised source and drain structures 904. The raised source and drain structures 904 can be grown on or above a substrate 910 of the wafer 900 using the epi-growth technique. The metrology device in this embodiment can measure the raised height H, pitches P, and/or widths W of the raised source and drain structures 904. Furthermore, through rotating the wafer 900, more information of the morphology of the wafer 900 can be obtained.

According to one embodiment, the metrology device is provided. The metrology device includes the light source and the image sensor. The light source is configured for providing the X-ray for illuminating the wafer. The image sensor is configured for detecting the spatial domain pattern produced when the X-ray illuminating the wafer.

In one or other embodiments, the metrology device further includes at least one of the lens group for focusing the X-ray to the wafer.

In one or other embodiments, the metrology device further includes the processor configured for obtaining the morphology of the wafer according to the detected spatial domain pattern.

In one or other embodiments, the metrology device further includes the Fourier's transformer and the processor. The Fourier's transformer is configured for transforming the detected spatial domain pattern into a Fourier frequency domain data. The processor is configured for obtaining the morphology of the wafer according to the Fourier frequency domain data.

In one or other embodiments, the processor is configured for obtaining the morphology of the metal layer of the wafer according to the detected spatial domain pattern.

In one or other embodiments, the processor is configured for obtaining the morphology of the dielectric layer of the wafer according to the detected spatial domain pattern.

In one or other embodiments, the processor is configured for obtaining the morphology of the semiconductor layer of the wafer according to the detected spatial domain pattern.

In one or other embodiments, the processor is configured for obtaining raised source and drain structures of the wafer according to the detected spatial domain pattern.

In one or other embodiments, the processor is configured for obtaining the morphology of at least one Fin field effect transistor (FinFET) of the wafer according to the detected spatial domain pattern.

In one or more embodiments, the metrology device further includes the rotation mechanism configured for rotating the wafer.

According to another embodiment, the metrology device is provided. The metrology device includes the electromagnetic radiation source and the image sensor. The electromagnetic radiation source is configured for providing electromagnetic radiation having the wavelength in the range of 0.01 to 10 nm for illuminating the wafer. The image sensor is configured for detecting the spatial domain pattern produced when the electromagnetic radiation illuminating the wafer.

In one or more embodiments, the metrology device further includes the lens group disposed between the electromagnetic radiation source and the image sensor.

In one or more embodiments, the metrology device further includes the Fourier's transformer and the processor. The Fourier's transformer is connected to the image sensor. The processor is connected to the Fourier's transformer.

According to yet another embodiment, the metrology method for measuring the morphology of the wafer is provided. The method includes the following acts of: (The acts are not recited in the sequence in which the acts are performed. That is, unless the sequence of the acts is expressly indicated, the sequence of the acts is interchangeable, and all or part of the acts may be simultaneously, partially simultaneously, or sequentially performed.)

The X-ray is provided to illuminate the wafer. The spatial domain pattern produced when the X-ray illuminating the wafer is detected.

In one or more embodiments, the metrology method further includes act:

focusing the X-ray to the wafer.

In one or more embodiments, the metrology method further includes act:

obtaining the morphology of the wafer according to the detected spatial domain pattern.

In one or more embodiments, the metrology method further includes act:

transforming the detected spatial domain pattern into a Fourier frequency domain data; and obtaining the morphology of the wafer according to the Fourier frequency domain data.

In one or more embodiments, the metrology method further includes act:

rotating the wafer.

In one or more embodiments, the metrology method further includes act:

obtaining the morphology of the wafer according to the detected spatial domain pattern.

In one or more embodiments, the metrology method further includes act:

obtaining raised source and drain structures of the wafer according to the detected spatial domain pattern.

Although the embodiments have been described in detail, it should be understood that various changes, substitutions and alterations can be made herein without departing from the spirit and scope of the embodiments as defined by the appended claims. For example, the wavelength of the X-ray 102 is not limited to the wavelength range mentioned above.

Moreover, the scope of the present application is not intended to be limited to the particular embodiments of the process, machine, manufacture, and composition of matter, means, methods, and steps described in the specification. A person having ordinary skill in the art can readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure. Accordingly, the scope of the present disclosure is defined by the appended claims rather than the foregoing description and the exemplary embodiments described therein.

What is claimed is:

1. A metrology device, comprising:
a light source configured to provide an X-ray;
at least one lens configured to focus the X-ray to a wafer that has a periodic structure, the focused X-ray passing through the wafer and being diffracted by the wafer;
an image sensor configured to detect the diffracted X-ray;
a Fourier's transformer configured to conduct a Fourier's transform of the diffracted X-ray detected by the image sensor; and
a processor configured to identify at least one peak from the Fourier's transform and to analyze the at least one peak to obtain a distance between layers of a transistor structure of the wafer.

2. The metrology device of claim 1, wherein the processor is further configured to obtain a morphology of the transistor structure of the wafer according to the Fourier's transform.

3. The metrology device of claim 1, further comprising:
a rotation mechanism configured to rotate the wafer.

4. A metrology device comprising:
an electromagnetic radiation source configured to provide electromagnetic radiation having a wavelength in the range of 0.01 to 10 nm;
at least one lens configured to focus the electromagnetic radiation to a wafer that has a periodic structure, the focused electromagnetic radiation passing through the wafer and being diffracted by the wafer;
an image sensor configured to detect the diffracted electromagnetic radiation;
a Fourier's transformer configured to conduct a Fourier's transform of the diffracted electromagnetic radiation detected by the image sensor; and
a processor configured to identify at least one peak from the Fourier's transform and to analyze the at least one peak to obtain a width of a layer of a transistor structure of the wafer.

5. The metrology device of claim 4, wherein the lens is disposed between the electromagnetic radiation source and the image sensor.

6. The metrology device of claim 4,
a wherein the Fourier's transformer is connected to the image sensor and the processor.

7. A metrology method for measuring the morphology of a wafer, comprising:
providing an X-ray;
focusing the X-ray to the wafer that has a periodic structure, the focused X-ray passing through the wafer and being diffracted by the wafer;
detecting the diffracted X-ray;
conducting a Fourier's transform of the detected diffracted X-ray;
identifying at least one peak from the Fourier's transform; and analyzing the at least one peak to obtain a height of a layer of a transistor structure of the wafer.

8. The metrology method of claim 7, further comprising:
obtaining a morphology of the transistor structure of the wafer according to the Fourier's transform.

9. The metrology method of claim 7, further comprising:
rotating the wafer.

10. The metrology method of claim 7, wherein a power of the X-ray is about 13 kW to 14 kW.

11. The metrology method of claim 7, wherein the focused X-ray passes through a back side of the wafer, and the transistor structure is over a side opposite to the backside of the wafer.

12. The metrology method of claim 7, further comprising providing the wafer that comprises a fin field effect transistor (finFET).

13. The metrology method of claim 7, wherein the X-ray is provided to illuminate the wafer along different incident angles.

14. The metrology device of claim 4, further comprising:
a rotation mechanism configured to rotate the wafer.

15. The metrology device of claim 1, wherein the X-ray has a frequency in the range of about 30 petahertz to about 30 exahertz.

16. The metrology device of claim 1, wherein each of the layers is one of a semiconductor layer, a metal layer, and a dielectric layer.

17. The metrology device of claim 4, wherein the layer is one of a semiconductor layer, a metal layer, and a dielectric layer.

18. The metrology method of claim 7, wherein the layer is one of a semiconductor layer, a metal layer, and a dielectric layer.

19. The metrology method of claim 7, wherein the X-ray is provided at a power greater than 12 kW.

20. The metrology method of claim 7, wherein the at least one peak corresponds to a period of the periodic structure of the wafer.

\* \* \* \* \*